United States Patent [19]

Hatton

[11] Patent Number: 4,884,457
[45] Date of Patent: Dec. 5, 1989

[54] MEANS AND METHOD FOR MONITORING THE FLOW OF A MULTI-PHASE PETROLEUM STREAM

[75] Inventor: Gregory J. Hatton, Houston, Tex.

[73] Assignee: Texaco Inc., White Plains, N.Y.

[21] Appl. No.: 327,873

[22] Filed: Mar. 23, 1989

Related U.S. Application Data

[63] Continuation of Ser. No. 102,943, Sep. 30, 1987, abandoned.

[51] Int. Cl.⁴ .................................................. G01F 1/74
[52] U.S. Cl. .................................................. 73/861.04
[58] Field of Search .................... 73/861.01–861.04, 73/861.05, 861.41

[56] References Cited

U.S. PATENT DOCUMENTS

| | | | |
|---|---|---|---|
| 4,402,230 | 9/1983 | Raptis | 73/861.04 |
| 4,429,581 | 2/1984 | Furmanga | 73/861.04 |
| 4,509,366 | 4/1985 | Matsushita et al. | 73/861.04 |
| 4,528,857 | 7/1985 | Bruner | 73/861.05 |
| 4,598,593 | 7/1986 | Sheen et al. | 73/861.04 |
| 4,604,904 | 8/1986 | Massen | 73/861.04 |

*Primary Examiner*—Stewart J. Levy
*Assistant Examiner*—Robert P. Bell
*Attorney, Agent, or Firm*—Robert A. Kulason; James J. O'Loughlin; Ronald G. Gillespie

[57] ABSTRACT

The multi-phase petroleum stream monitor includes two densitometers which measure the density of the petroleum stream at two locations and provides corresponding signals. The temperature and the pressure of the petroleum stream are also measured and corresponding signals provided. Apparatus provides signals corresponding to the density of the liquid in the petroleum stream and to the density of the gas in the petroleum stream. The liquid flow rate and the gas flow rate of the petroleum stream are determined in accordance with the two sensed density signals, the temperature signal, the pressure signal, the liquid density signal and the gas density signal.

14 Claims, 2 Drawing Sheets

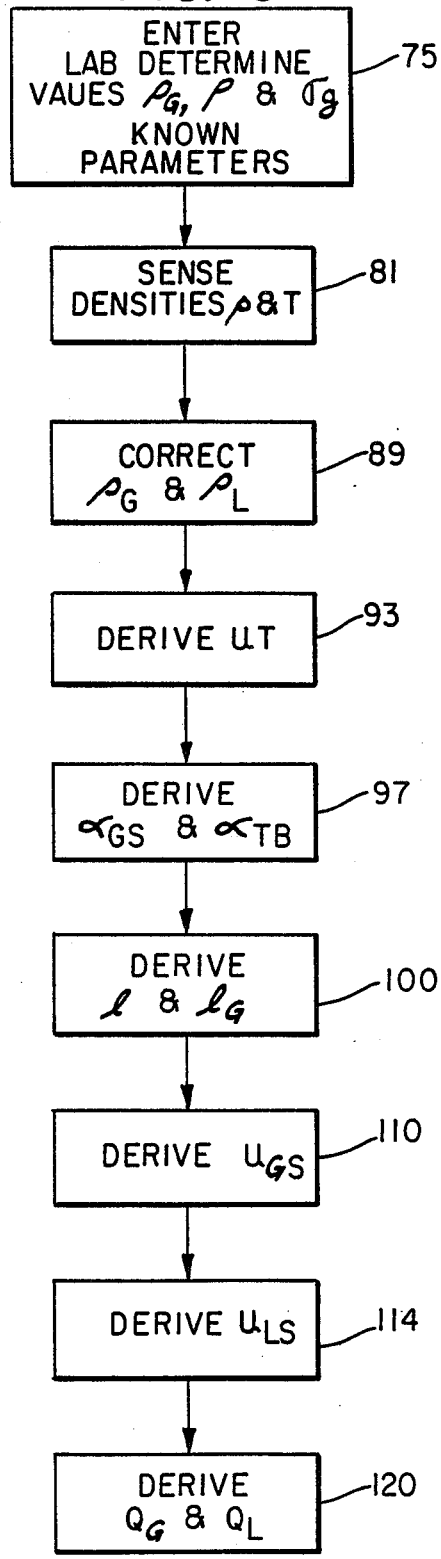

MEANS AND METHOD FOR MONITORING THE FLOW OF A MULTI-PHASE PETROLEUM STREAM

This is a continuation of application Ser. No. 102,943, filed Sept. 30, 1987, now abandoned.

BACKGROUND OF THE INVENTION

Field of the Invention

The present invention relates to monitoring of a petroleum stream in general and, more particularly, to monitoring the flow of a multi-phase petroleum stream.

SUMMARY OF THE INVENTION

The multi-phase petroleum stream monitor includes two densitometers which measure the density of the petroleum stream at two locations and provides corresponding signals. The temperature and the pressure of the petroleum stream are also measured and corresponding signals provided. Apparatus provides signals corresponding to the density of the liquid in the petroleum stream and to the density of the gas in the petroleum stream. The liquid flow rate and the gas flow rate of the petroleum stream are determined in accordance with the two sensed density signals, the temperature signal, the pressure signal, the liquid density signal and the gas density signal.

The objects and advantages of the invention will appear more fully hereinafter from a consideration of the detailed description which follows, taken together with the accompanying drawings wherein one embodiment of the invention is illustrated by way of example. It is to be expressly understood, however, that the drawings are for illustration purposes only and are not to be construed as defining the limits of the invention.

DESCRIPTION OF THE DRAWINGS

FIG. 3 is a flow diagram of steps utilizing the computer means shown in FIG. 1 to arrive at the flow rates for the gas and the liquid in the petroleum stream.

DESCRIPTION OF THE INVENTION

Figure 1:
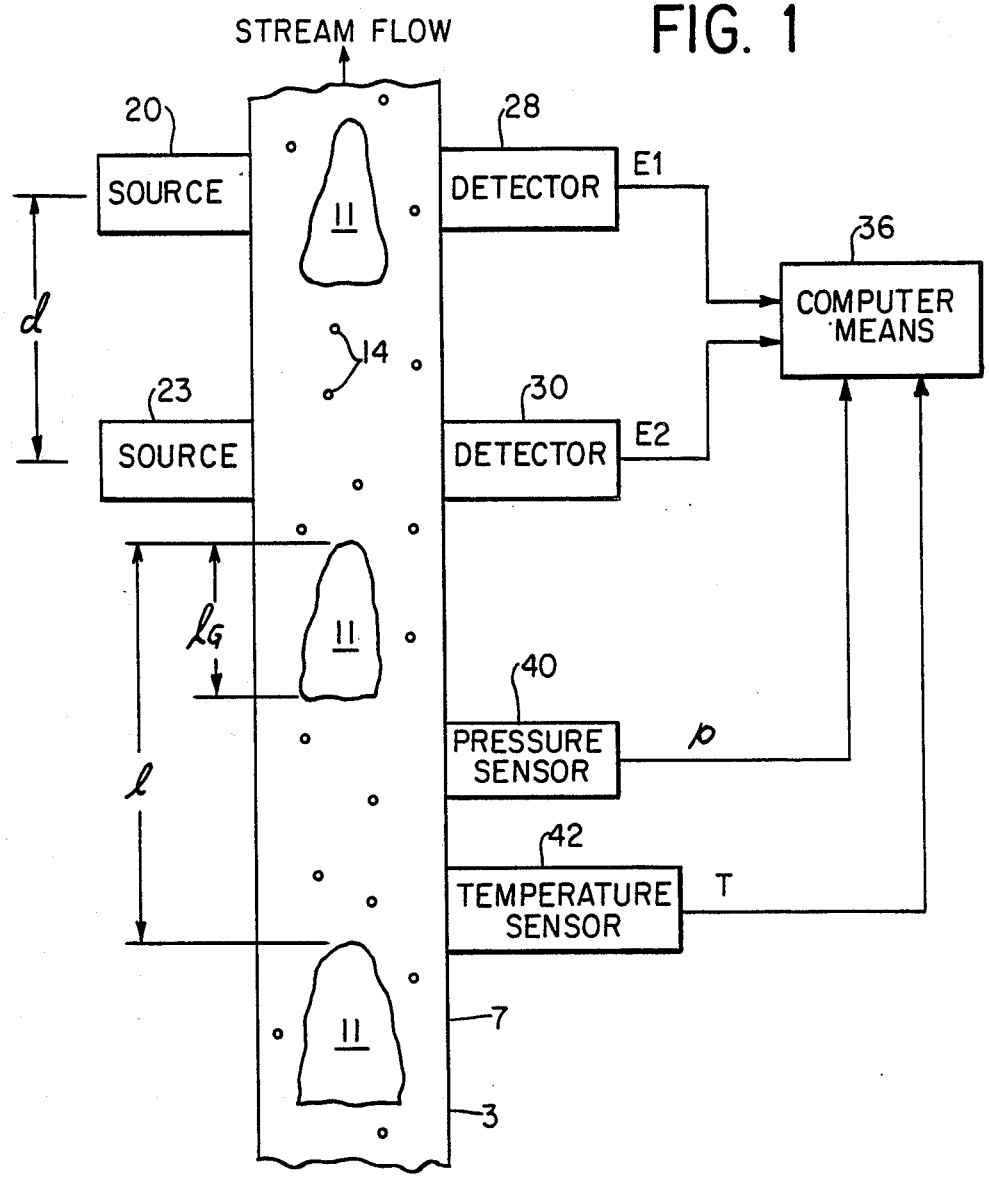
FIG. 1 is a simplified block diagram of a multi-phase petroleum stream monitor constructed in accordance with the present invention.

The present invention monitors the gas flow rate and the liquid flow rate of a multi-phase petroleum stream utilizing well known equations. The following Table I relates terms of the equations and their definitions:

TABLE I $U_T$ = velocity of large gas bubbles
$U_{GS}$ = gas superficial velocity
$U_{LS}$ = liquid superficial velocity
A = cross-sectional area of pipe
$A_G$ = cross-sectional area of gas bubble
$l_G$ = length of gas bubble
$l$ = length from end of one bubble to end of next bubble
$l_{LS}$ = fraction of gas in liquid slug section
$\alpha_{TB}$ = fraction of gas in gas bubble section
QG = gas flow rate
QL = liquid flow rate
$\rho_G$ = density of gas
$\rho_L$ = density of liquid
$\sigma_g$ = surface tension of gas
D = diameter of pipe
g = acceleration of gravity
p = pressure

TABLE I-continued

T = temperature

The equations disclosed in A. E. Dukler's course on gas-liquid flow given at the University of Houston, Houston, Tex., lead to equation 1:

$$U_{GS}A = [A_G \rho_G + A(l - l_G)\alpha_{LS}]/(\rho/U_T) \quad 1.$$

Equation 1 may be rewritten as equation 2 following:

$$U_{GS} = [\rho_G \alpha_{TB} + (\rho - \rho_G)\alpha_{LS}]/(\rho/U_T) \quad 2.$$

Equation 3 written as follows:

$$U_T = 1.2(U_{LS} + U_{GS}) - [\sigma_g(\rho_L - \rho_G)/\rho_L^{2\frac{1}{4}}] + .35\sqrt{gD} \quad 3.$$

$$U_{LS} = \{U_T + [\sigma_g(\rho_L - \rho_G)/\rho_L^2]^{\frac{1}{4}} - .35\sqrt{gD} - 1.2U_{GS}\}/1.2 \quad 4.$$

From the superficial velocities $U_{GS}$ and $U_{LS}$ of the gas and the liquid, respectively, the flow rate of the gas $Q_G$ and the flow rate $Q_L$ of the liquid can be determined from equations 5 and 6, following:

$$Q_G = (U_{GS})A_G \quad 5.$$

$$Q_L = (U_{LS})(A - A_G) \quad 6.$$

Thus in vertical flow which is shown in FIG. 1, there is shown a petroleum stream 3 flowing in a pipe 7. Within petroleum stream 3 there are gas bubbles 11 and further within the liquid slugs there is dispersed gas 14. A liquid slug is that portion of the petroleum stream between two bubbles.

In this particular example, there is shown sources 20 and 23 of gamma energy which provide beams across petroleum stream 3 where they are detected by detectors 28 and 30, respectively. Although the present example shows a slug detector as being composed of a gamma ray source with a gamma ray detector, other types of slug detectors may be used to determine the density of the liquid flowing past a particular point. For example X-ray sources and sensors, ultrasonic sources and sensors are some. Further, sources 20 and 23 are located a predetermined distance d apart. Detectors 28, 30 provide density signals E1 and E2, respectively, to computer means 36. Computer means 36 may be a general purpose digital computer.

A pressure sensor 40 and a temperature sensor 42 senses the pressure and temperature of petroleum stream 3, respectively, and provides a pressure signal p and a temperature signal T, respectively, to computer means 36.

Also shown in FIG. 1, for purposes of explanation, length $\rho_G$ is graphically defined as the length of a bubble and length $\rho$ as being the distance from the start of one bubble to the start of the next subsequent bubble.

Figure 2:
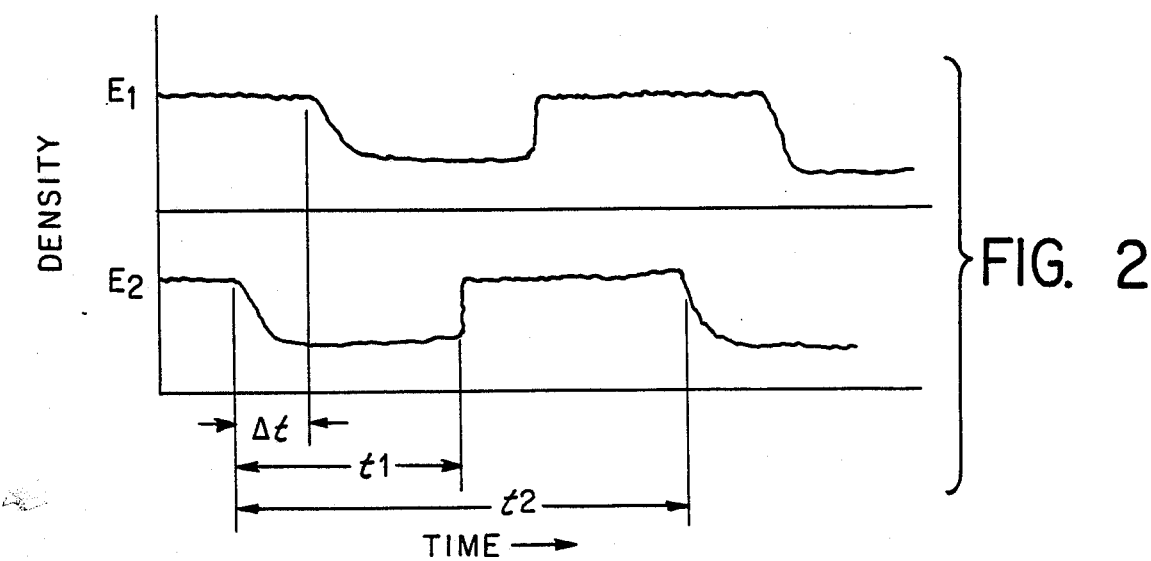
FIG. 2 represents waveforms of signals E1 and E2 provided by the detectors shown in FIG. 1.

FIG. 2 shows two plots of signals E1 and E2 of density versus time. For the purpose of explaining various times used in the specification, $\Delta t$ is shown as the time differential between the leading edge of a bubble passing detector 30 and its subsequent passage of detector 28. It is obvious that $\Delta t$ with the known distance d can be used to derive the velocity $U_T$ of the gas bubble.

Further, t1 defines the time for length of passage of a gas bubble, while t2 defines the time from the start of one gas bubble to the start of the next subsequent gas bubble.

With reference to the flow diagram of FIG. 3, values for the Lab determined density of the gas, density of the liquid and the surface tension of the gas are entered into computer means 36. Computer means 36 then senses the densities of the petroleum signals in accordance with signals E1 and E2. The pressure of the petroleum stream in accordance with signal p and the temperature of the petroleum stream in accordance with signal t. The pressure signal p and temperature signal t are used to correct the densities $\rho_L$ and $\rho_G$ already entered into computer means 36 as is shown in block 89. The next step is to derive $U_T$ (per block 93) from the simple expediency of dividing the distance d by $\Delta t$.

In block 97 computer means 36 is programmed to derive $\alpha_{LS}$ and $\alpha_{TB}$. As noted, $\alpha_{LS}$ is the fraction of gas in the liquid slug and $\alpha_{TB}$ is the fraction of gas in the gas bubble. Density signals E1 and E2 are used in this derivation and results from calibration data taken wherein the densities of the various composition of liquid and gas in the pipe are determined as stored in computer means 36 memory.

Block 100 provides for the derivation of the terms l and $l_G$ which is accomplished by computer means 36. By knowing the value for $U_T$, computer means 36 can then use its internal clock to determine $l_G$ and l. Block 110 pertains to the deriving of the gas superficial velocity $U_{GS}$ utilizing equation 2. Block 114 provides for computer means 36 to derive the liquid superficial velocity $U_{LS}$.

The final step in block 120 is to derive the gas flow rate $Q_G$ and the liquid flow rate $Q_L$ in accordance with equations 5 and 6, respectively. Although FIG. 1 doesn't show it, computer means 36 may be providing an output to recording means to record the data.

The present invention may also be used for horizontal flow wherein equation 3 is rewritten as $$U_T = C(U_{LS} + U_{GS}) - U_O \qquad 7.$$

where C is a constant having a value in a range of 1.2 to 1.3, and $U_O$ is a substantially constant velocity determined by lab flow calibration.

What is claimed is:

1. Apparatus for monitoring a multi-phase petroleum stream flowing in a pipe comprising:
   two density sensing means for sensing the density of the petroleum stream at two locations a known distance apart and providing sensed density signals, corresponding to the sensed densities and which are related to a fluid velocity of the petroleum stream,
   temperature sensing means for sensing the temperature of the petroleum stream and providing a temperature signal representative of the sensed temperature,
   pressure sensing means for sensing the pressure of the petroleum stream and providing a pressure signal in accordance with the sensed pressure, and
   flow rate means connected to both density sensing means, to the pressure sensing means and to the temperature sensing means for entering known values of gas density liquid density and a surface tension of gas and for providing signals corresponding to the liquid flow rate and to the gas flow rate of the petroleum stream in accordance with the sensed density signals, the temperature signal, the pressure signal and entered known values of the gas and the liquid.

2. Apparatus as described in claim 1 in which the flow rate means includes:
   correction means connected to the temperature sensing means and the pressure sensing means for providing a corrected liquid density signal and a corrected gas density signal corresponding to the liquid density and the gas density, respectively, corrected for the temperature and the pressure of the petroleum stream in accordance with the entered values, density the temperature signal and the pressure signal.

3. Apparatus as described in claim 2 in which the flow rate means includes:
   gas superficial velocity means connected to the correction means and to both density sensing means for providing a signal corresponding to the superficial velocity of the gas in the petroleum stream in accordance with the sensed density signals from both density sensing means.

4. Apparatus as described in claim 3 in which the gas superficial velocity means includes:
   means connected to both density sensing means for deriving the velocity of the petroleum stream in accordance with the sensed density signals from the density sensing means,
   means connected to both density sensing means for deriving the fraction of gas in a liquid slug and the fraction of gas in a gas bubble in accordance with the sensed density signals, and
   means connected to at least one of the density sensing means for deriving the distance from the end of one gas bubble to the end of the next gas bubble and the length of a gas bubble in accordance with a sensed density signal from the density sensing means.

5. Apparatus as described in claim 4 in which the superficial gas velocity means includes:
   network means connected to the stream velocity means, to the gas fraction means and to the length means for providing the superficial gas velocity signal in accordance with the stream velocity signal, the gas fraction in a slug signal, the gas fraction of a bubble signal, the length from the point of one bubble to the corresponding point of another bubble, and the length of a bubble signal.

6. Apparatus as described in claim 5 in which the flow rate means includes:
   superficial liquid velocity means connected to the gas superficial velocity means, to the correction means and to the network means for providing a signal corresponding to the superficial liquid velocity in accordance with the stream velocity signal, the corrected liquid density signal, the corrected gas density signal and the superficial gas velocity signal.

7. Apparatus as described in claim 6 in which the flow rate means includes:
   circuit means connected to the network means and to the superficial liquid velocity means for providing signals corresponding to the flow rate of the gas in the petroleum stream and to the flow rate of the liquid in the petroleum stream in accordance with the superficial liquid velocity signal and the superficial gas velocity signal.

8. A method of monitoring a multi-phase petroleum stream flowing in a pipe comprising the steps of:
sensing the density of the petroleum stream at two locations a known distance apart,
providing sensed density signals corresponding to the sensed densities and which are related to the fluid velocity of the petroleum stream,
sensing the temperature of the petroleum stream and providing a temperature signal representative of the sensed temperature,
sensing the pressure of the petroleum stream and providing a pressure signal in accordance with the sensed pressure,
determining a density of the liquid in the petroleum stream,
determining a surface tension of gas in the petroleum stream,
determining a density of the gas in the petroleum stream, and
providing signals corresponding to the liquid flow rate and to the gas flow rate of the petroleum stream in accordance with the sensed density signals, the temperature signal, the determined liquid density, the determined gas surface tension and the determined gas density.

9. A method as described in claim 8 in which the flow rate step includes:
providing signals corresponding to the liquid density and the gas density corrected for the temperature and the pressure of the petroleum stream in accordance with the sensed density signals, the temperature signal and the pressure signal.

10. A method as described in claim 9 in which the flow rate step includes:
providing a gas superficial velocity signal corresponding to the superficial velocity of the gas in the petroleum stream in accordance with the sensed density signals.

11. A method as described in claim 10 in which the gas superficial velocity step includes:
deriving the velocity of the petroleum stream in accordance with the sensed density signals,
deriving the fraction of gas in the liquid slug and the fraction of gas in a gas bubble in accordance with the sensed density signals, and
deriving the distance from the end of one gas bubble to the end of the next gas bubble and the length of a gas bubble in accordance with at least one of the sensed density signals.

12. A method as described in claim 11 in which the superficial gas velocity step includes:
providing the superficial gas velocity signal in accordance with the stream velocity signal, the gas fraction in a slug signal, the gas fraction of a bubble signal, the length from the point of one bubble to the corresponding point of another bubble signal, and the length of a bubble signal.

13. A method as described in claim 12 in which the flow rate step includes:
providing a signal corresponding to the superficial liquid velocity in accordance with the stream velocity signal, the corrected density liquid signal, the corrected gas density signal and the superficial gas velocity signal.

14. A method as described in claim 13 in which the flow rate step includes:
providing signals corresponding to the flow rate of the gas in the petroleum stream and to the flow rate of the liquid in the petroleum stream in accordance with the superficial liquid velocity signal and the superficial gas velocity signal.

* * * * *